United States Patent
Li et al.

(10) Patent No.: US 8,350,033 B2
(45) Date of Patent: Jan. 8, 2013

(54) 4-((3, 5, 6-TRIMETHYLPYRAZINE-2-YL) METHOXYL) BENZOIC ACID AND ITS DERIVATIVES

(76) Inventors: Jiaming Li, Hefei (CN); Guangwei He, Hefei (CN); Yonghai Zhao, Hefei (CN); Fengshi Ma, Hefei (CN); Yong He, Hefei (CN); Qiang Wu, Hefei (CN); Feng Li, Hefei (CN)

( * ) Notice: Subject to any disclaimer, the term of this patent is extended or adjusted under 35 U.S.C. 154(b) by 42 days.

(21) Appl. No.: 12/681,623

(22) PCT Filed: Oct. 27, 2008

(86) PCT No.: PCT/CN2008/072840
§ 371 (c)(1),
(2), (4) Date: Apr. 5, 2010

(87) PCT Pub. No.: WO2009/056070
PCT Pub. Date: May 7, 2009

(65) Prior Publication Data
US 2010/0228029 A1    Sep. 9, 2010

(30) Foreign Application Priority Data
Oct. 26, 2007    (CN) .......................... 2007 1 0163477

(51) Int. Cl.
*C07D 241/00*    (2006.01)
(52) U.S. Cl. ...................................... 544/410
(58) Field of Classification Search ............. 544/410
See application file for complete search history.

(56) References Cited

FOREIGN PATENT DOCUMENTS

| CN | 1424313 | 6/2003 |
|---|---|---|
| CN | 101012201 | 8/2007 |
| CN | 101143851 | 3/2008 |

OTHER PUBLICATIONS

Jordan, V. C. Nature Reviews: Drug Discovery, 2, 2003, 205.*
Hackam, et al. JAMA, 296(14), 2006, 1731-1732.*
Ren, Mei et al. Synthesis and THE-1 inhibitory activity of ligustrazine derivatives. Chinese Chemical Letters, May 2007, vol. 18, No. 5, pp. 539-541, ISSN: 1001-8417 p. 540, table 1, Scheme 1.
Chen, Xianchao et al. Structural modification of ligustrazine. Progress in Pharmaceutical Sciences, 2005, vol. 29, No. 6, pp. 241-246.
Xia, Chengjian et al. Rearch on anticoagulation activity of ligustrazine and ligustrazine derivatives. Chinese Herbal Medicines Aug. 2004, vol. 35 No. 8, pp. 911-913.
Xue, Peng et al. Synthesis and characterization of ligustrazine-piperazidine. Chinese Chemical Reagents Sep. 2006, vol. 28, No. 9,pp. 513-515.
Chen, Xianchao et al. Recent advances in the structural modification of ligustrazine and cerebro/cardiovascular activity of ligustrazine derivatives. Drugs of the Future, 2005, vol. 30, No. 10, pp. 1059-1065.
Liu, Xinyong et al. Synthesis of the novel liqustrazine derivatives and their protective effect on injured vascular endothelial cell damaged hydrogen peroxide. Bioorganic & Medicinal Chemistry Letters, 2003, vol. 13, No. 13, pp. 2123-2126.
Chen, Xianchao et al. Design, synthesis, and biological activities of novel ligustrazine derivatives. Bioorganic & Medicinal Chemistry, 2007, vol. 15, No. 1o, pp. 3315-3320.

* cited by examiner

*Primary Examiner* — Douglas M Willis

(57) ABSTRACT

Ligustrazine aromatic acid ether derivative of general formula I, its preparation method, pharmaceutical composition and application, wherein Ar is selected from aryl substituted aryl and substituted styryl, R is selected from hydrogen and alkyl with no more than 6 carbon atoms.

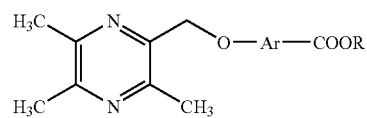

I

11 Claims, No Drawings

4-((3, 5, 6-TRIMETHYLPYRAZINE-2-YL) METHOXYL) BENZOIC ACID AND ITS DERIVATIVES

CROSS REFERENCE OF RELATED APPLICATION

This is a U.S. National Stage under 35 U.S.C 371 of the International Application PCT/CN2008/072840, filed Oct. 27, 2008, which claims priority under 35 U.S.C. 119(a-d) to CN 200710163477.1, filed Oct. 26, 2007.

BACKGROUND OF THE PRESENT INVENTION

1. Field of Invention

The present invention relates to a medicine of ligustrazine aromatic acid ether derivative for treating cardiovascular and cerebrovascular diseases, its preparation method, and medical compositions thereof, belongs to the field of pharmaceutical technology.

2. Description of Related Arts

Cardiovascular and cerebrovascular diseases are common diseases and frequently encountered diseases that harm people's health seriously, and has increasing incidence rate along with the aging of population. According to statistics, 16 million people die of various cardiovascular and cerebrovascular diseases each year, which is the first killer threatening human's health.

Thrombembolia is an important factor that causes cardiovascular and cerebrovascular diseases, coronary artery diseases and related ischemic complications may cause several clinic syndromes such as apoplexy, miocardial infarction and peripheral arterial disease, and the main reason is that the thrombus formed in the artery blocks the blood vessel and causes serious ischemia. Thromboembolic diseases, which has coronary artery thrombosis and cerebral thrombosis as core, has very high incidence rate and death rate in China. Therefore, it is the most popular research subject to prevent thrombus in the field of angiocardiopathy. At present, there are mainly three types of anticoagulants, platelet aggregation inhibitors and thrombolytic drugs for treating thrombotic diseases. Anticoagulants are generally drugs of low molecular weight including heparin drugs such as heparin sodium, coumarin drugs such as Warfarin, genetic recombined hirudin drugs such as Lepirudin and Bivalirudin, and polysaccharide sulfate. Platelet aggregation inhibitors can limit developing and embolizing of the thrombus in artery and vein, but can not prevent the artery thrombosis led by blood platelet. This type of drugs mostly have side effect of delayed hemorrhage. Thrombolytic drugs are generally biotechnical products, including streptokinase, urokinase, tissue-type plasminogen activator, duteplase, moteplase, and so on. This type of drugs can dissolve formed blood clot, so as to provide a fast and practical method for eliminating cardiovascular thrombus and cerebrovascular thrombus, establishing reperfusion of blood, saving dying cardiac muscle and brain tissue. However, this type of drugs have high requirement of purifying technology, and their products may have antigenicity to induce anaphylactic reaction. Some products may interfere coagulation function, and therefore has a danger of causing hemorrhage. Platelet aggregation inhibitors generally prevent forming and developing of thrombus by inhibiting aggregation of the platelet. Inhibitors of platelet aggregation can be classified into platelet activating factor (PAF) antagonist, inhibitor of thromboxane synthase and receptor antagonist, thrombin active site inhibitor, inhibitor of 10A factor, glycoprotein receptor IIb/IIIa (GPIIb/IIIa) antagonist, and so on. Besides Aspirin, Ticlopidine and Ozagrel, which are clinically used for years, this type of drugs include Abciximab, Argatroban, and Tirofiban, which has high bioactivity and relatively less side effect, but also has a danger of delayed hemorrhage. For overcoming the drawbacks of the foregoing drugs, it is still a hotspot of drug research to develop new-type, highly efficient and lowly toxic treating drugs for cardiovascular and cerebrovascular diseases. China has abundant natural resources of traditional Chinese medicinal materials, and it is of great theoretic significance and clinic application value to filter out components which can inhibit aggregation of platelet as lead compounds, and then process proper drug design and synthesization on the lead compounds by modern pharmacochemistry principles, so as to filter out drugs for treating thromboembolic diseases, which have better therapeutic effect, less side effects, higher bioavailability, and longer half time.

The design principle of the present invention is as follows:

Ozagrel and UK37248 are highly selective TXA2 synthetase inhibitors, and have very high antiplatelet aggregative activity, referring to Lizuka. K, Akahane. K, Momose. D, et al. Highly selective inhibitors of thromboxane synthetase. 1. Imidazole Derivatives. J. Med. Chem. 1981, 24(10): 1139-1148. Ozagrel and UK37248 can inhibit foming of cerebral thrombosis and cerebrovascular spasm, and are generally applied in treating acute cerebral infarction, coronary heart disease and angina, referring to Song Bo, Jiang Congqing, Cao chuanbin et al. Clinic research on treating unstable angina pectoris with sodium ozagrel. Chinese Journal of General Practitioners, 2006, 5(4): 255-256. And Wu Jinying. Clinical observation of 42 samples on treating acute cerebral infarction with sodium ozagrel. The structures of Ozagrel and UK37248 are as follows:

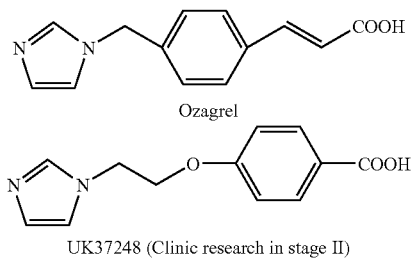

Ozagrel

UK37248 (Clinic research in stage II)

The dry rhizome of Ligusticum Wallichii Franch, which belongs to Apiaceae, is a kind of Chinese medicinal herb proved to be of great therapeutic effect by Chinese medical practice, has the function of promoting circulation of blood and Qi, eliminating bruise and relieving pain, and has been applied in treating ischemic cardiovascular and cerebrovascular diseases. Ligustrazine (Lig) is the main active component in Ligusticum Wallichii Franch, and its chemical name is 2,3,5,6-Tetramethylpyrazine, called Tetramethylpyrazine (TMP) for short. Its structure is as below:

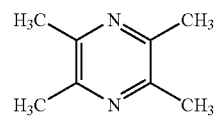

According to the pharmacological research, Ligustrazine can dilate vessel, inhibit aggregation of platelet, prevent forming of thrombus, alleviate cerebral ischemia, referring to He Jing. Pharmacological effect and clinical application of Ligustrazine. Beijing medicine, 2005, 23: 31-32, and Wang yanping, Li Wenlan, Fan Yuqi. Progress of pharmacological effect of Ligustrazine. Orug Evaluation yao pin pingjia, 2006, 3(2): 144-150.

Ferulic acid is the active component of the Chinese medicinal herb including Angelica and Ligusticum Wallichii Franch. Its structure is as below:

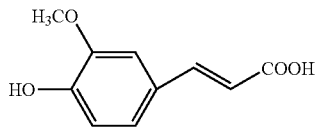 [SMILES: COc1cc(/C=C/C(=O)O)ccc1O]

According to the pharmacological research, Ferulic acid has the function of inhibiting aggregation of platelet, inhibiting releasing of 5-hydroxytryptamine from platelet, prevent forming of vein bypass thrombus, resisting atherosclerosis, anti-oxidation and enhancing immunologic function, referring to Ou shiyi, Bao Huiyan, Lan Zhidong. Progress of pharmacological effect of Ferulic acid and its derivatives. Journal of Chinese Medicinal Materials, 2001, 24(3): 220-221.

To searching for more effective ligustrazine compound, the present invention uses ligustrazine and ferulic acid as lead compounds, uses Ozagrel and UK37248 as model compounds according to the bioisosterism in pharmacochemistry, designs and synthesizes the Ligustrazine aromatic acid ether derivative according to the present invention, which is found to be highly efficient, lowly toxic and highly selective.

SUMMARY OF THE PRESENT INVENTION

An object of the present invention is to provide a Ligustrazine aromatic acid ether compound or a medicinal salt thereof:

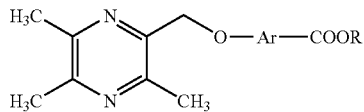

Particularly, Ar is selected from aryl, substituted aryl or substituted styryl, and R is selected from H or alkyl containing no more than 6 carbon atoms.

Particularly, Ar is selected from phenyl, 3,5-dimethoxyphenyl, 3-methoxyphenyl, 4-methoxyphenyl, styryl, 3-methoxy styryl, halogen-substituted phenyl, naphthyl, furyl, and thiazyl, and R is selected from H, —CH$_3$, and —CH$_2$CH$_3$.

The following compounds are preferred: 4-((3,5,6-trimethylpyrazine-2-yl)methoxyl)benzoic acid (MC1), (E)-3-(4-((3,5,6-Trimethylpyrazin-2-yl)methoxy)-3-methoxyphenyl) acrylic acid (MC2), and 3-((3,5,6-trimethylpyrazine-2-yl) methoxyl)-4-methoxybenzoic acid (MC5).

Structural formula of typical compounds are as follow:

TABLE 1 number and structure of ligustrazine aromatic acid ether derivatives

| No. | structure |
|---|---|
| MC1 | |
| MC2 | 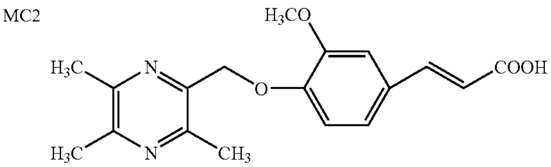 |
| MC3 | 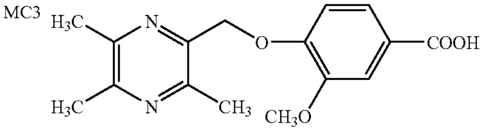 |
| MC4 | 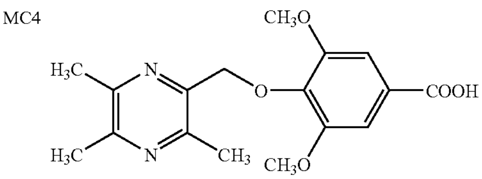 |
| MC5 | 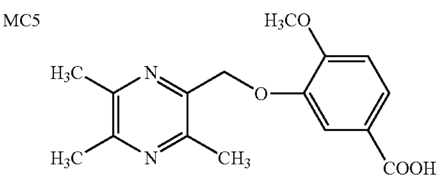 |
| MC6 | 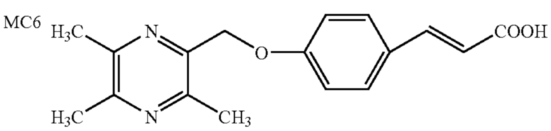 |

The medicinal salt of the compound according to the present invention, is selected from alkali metal salts, alkaline-earth salts, salts formed by amino acid or alkaline compounds containing amido, or medicine-allowed salts formed by mineral acid or organic acid, preferably, is selected from kali salt, sodium salt, ammonium salt, or salt formed by hydrochloric acid, sulphuric acid, citric acid or maleic acid.

The present invention also comprises medical compositions containing the compound or the medicinal salt according to the present invention. The compositions according to the present invention contain the foregoing ligustrazine aromatic acid ether derivatives and the medicinal salts thereof. The ligustrazine aromatic acid ether derivatives and the medicinal salts thereof and excipient are prepared to be drugs of different dosage forms.

The present invention also includes applying the compounds or the medicinal salts thereof according to the present invention to treat or prevent cardiovascular and cerebrovascular diseases, including preventing aggregation of platelet and treating or preventing thromboembolic diseases.

A process for preparing the compounds or the medicinal salts thereof according to the present invention, comprises the steps of:

(1) dissolving intermediates including substituted hydroxy aromatic acid ester and 2-bromomethyl-3,5,6-trimethylpyrazine into an organic solution, preferably DMF or acetone; adding inorganic base or organic base, preferably K$_2$CO$_3$, Na$_2$CO$_3$, ET$_3$N; heating up to 80-95° C., stirring to react for 6-12 h, filtering, adding water into a filtrate directly or after the solution has been distilled out under reduced pressure, extracting with organic solution, drying, recycling the organic solution under reduced pressure to obtain an oily matter, separating and purifying the oily matter to obtain a ligustrazine aromatic acid ester ether derivative, dissolving the obtained ligustrazine aromatic acid ester ether derivative into alcohol or methanol-water mixture, adding an inorganic base to hydrolyze, preferably NaOH or KOH, distilling the alcohol or the methanol under reduced pressure after hydrolyzation, neutralizing to pH 4-5 with dilute hydrochloric acid while keeping water phase cool, separating out solid, processing with vacuum filtration, washing the solid with cool water, recrystallizing with anhydrous alcohol after vacuum filtration to obtain a ligustrazine aromatic acid ether derivative;

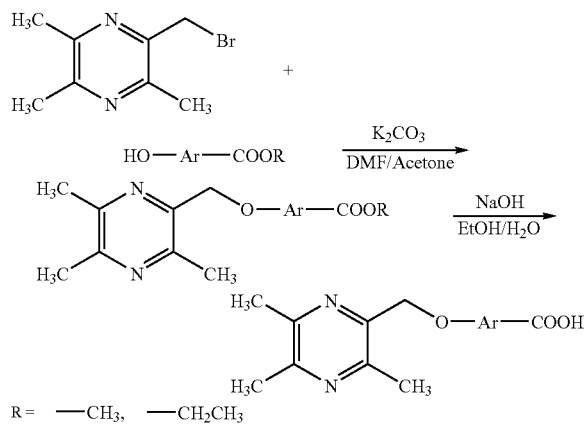

(2) reacting the compound with a base or an acid to obtain a salt.

The intermediate, 2-bromomethyl-3,5,6-trimethylpyrazine, is prepared by the following process: dissolving anhydrous ligustrazine, NBS and benzoperoxide into $CCl_4$, under irradiation of an incandescent lamp, heating, reacting for 10 h under circumfluence, wherein the reaction solution appears purple after reaction finishes, filtering out generated succinimide to obtain purple filtrate, recycling the $CCl_4$ under reduced pressure to obtain a purple viscous liquid, distilling under reduced pressure, collecting a cut fraction under 99-101° C./2 mmHg to obtain colorless liquid of 2-bromomethyl-3,5,6-trimethylpyrazine, m.p. 41.2-44° C.

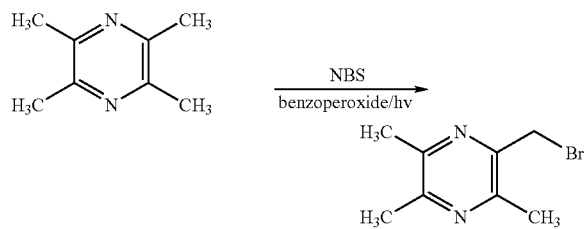

When the Ar is styryl, or 3-methoxy styryl, a process for preparing the compounds according to the present invention, comprises the steps of:

dissolving substituted hydroxy aromatic aldehyde, and 2-bromomethyl-3,5,6-trimethylpyrazine into an organic solution, preferably DMF or acetone; adding inorganic base or organic base, preferably $K_2CO_3$, $Na_2CO_3$, $ET_3N$; heating up to 80-95° C., stirring to react for 6-12 h, filtering, adding water into a filtrate directly or after the solution has been distilled out under reduced pressure, extracting with organic solution, drying, recycling the organic solution under reduced pressure to obtain an oily matter, separating and purifying the oily matter to obtain a ligustrazine aromatic aldehyde ether derivative, adding the obtained ligustrazine aromatic aldehyde ether derivative, malonic acid, pyridine, benzene, and piperidine of catalytic amount into a reactor, stifling, heating, reacting under circumfluence, eliminating water with an oil-water separator during reacting, cooling to 80° C. after reaction finishes, adding 30% $K_2CO_3$ solution, stifling for 30 min, cooling the reaction solution to room temperature, separating out a layer of benzene, adjusting a water phase to about pH 4 with hydrochloric acid, separating out solid, washing the solid with cool water, processing with vacuum filtration, recrystallizing with anhydrous alcohol to obtain a ligustrazine aromatic acid ether derivative.

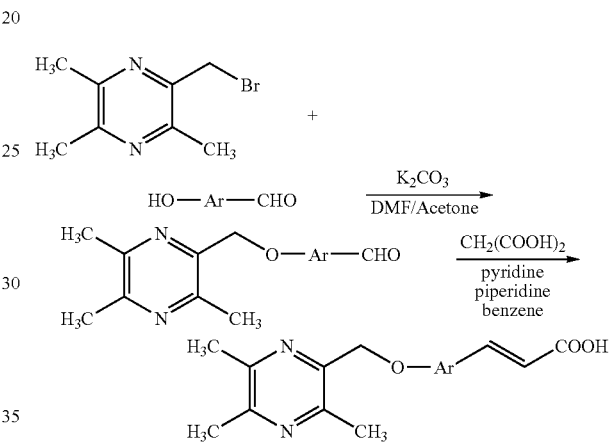

The beneficial effects of the compounds according to the present invention is illustrated by the following experimental data.

Experiment of resisting platelet aggregation with the ligustrazine aromatic acid ether derivatives: Anaesthetizing intravenously a rabbit with 3% pentobarbital sodium, separating arteria carotis communis and taking blood by inserting a pipe, using 3.8% sodium citrate solution (dissolving 3.8 g sodium citrate with distilled water, up to 100 mL, filtering, bottling, sterilizing under 121° C. and high pressure for 15 min) as an anticoagulant (1:9), 1000 r/min, centrifuging for 5 min to prepare platelet-rich plasma (PRP), 3000 r/min, centrifuging for 15 min to prepare platelet-poor plasma (PPP). Cultivating the PRP under 37° C. in a silicified cuvette for 5 min, measuring absorbance (A) at 600 nm, adjusting the absorbance of the PRP to 0.6-0.7 with the PPP, adding 1.7 mL adjusted PRP into another silicified cuvette, adding 200 μL of the test drug, measuring the absorbance at 600 nm before adding collagen, then adding 100 μL of ADP (final concentration of 4 μmol/L), respectively measuring the absorbance when 2 and 5 min after adding the ADP, calculating aggregation rate (AR) by the following formula: AR=(A before adding the ADP−A after adding the ADP)/A before adding the ADP (100%.). At the same time, calculating aggregation inhibition rate (AIR) of the tested drug to platelet: AIR=[1−(aggregation percentage in administrated tube/aggregation percentage in contrast tube)]×100. Calculating 50% inhibitory concentration ($IC_{50}$) of the tested drug, referring to table 2.

TABLE 2 effect of ligustrazine aromatic acid ether
derivatives to aggregation of platelet

| Compd | IC$_{50}$(mmol/L) |
| --- | --- |
| MC$_1$ | 1.36 |
| MC$_2$ | 0.28 |
| MC$_3$ | —* |
| Ozagrel (contrast) | 1.60 |
| MC$_4$ | —* |
| MC$_5$ | 1.00 |
| MC$_6$ | —* |

—*: the compound does not have antiplatelet aggregative activity.

The experiment of resisting platelet aggregation with the ligustrazine aromatic acid ether derivatives shows that, the antiplatelet aggregative activity of MC$_1$, MC$_2$, and MC$_5$ are all stronger than Ozagrel positive drug, wherein the antiplatelet aggregative activity of MC$_2$ is 5.7 times of Ozagrel, showing that polymer of ligustrazine and ferulic acid has high antiplatelet aggregative activity.

The experiment shows that the ligustrazine aromatic acid ether derivatives according to the present invention has higher efficiency, lower toxin and higher selectivity as comparing to prior art.

DETAILED DESCRIPTION OF THE PREFERRED EMBODIMENT

Instruments: LCQ ADVANTAGE MAX Liquid chromatography-mass spectrograph (LC-MS), FINNIGAN corporation; Nicolet Avatar370DTGS infrared spectrometer, Therm-Electron corporation; Bruker 300 MHz NMR spectrometer with superconducting magnet, wherein an interior label is TMS, solution is CDCl$_3$, DMSO-d$_6$; WRS-1B number melting point detector, SHANGHAI PRECISION & SCIENTIFIC INSTRUMENT CO., LTD.; SGW X-4 micro melting point apparatus, SHANGHAI PRECISION & SCIENTIFIC INSTRUMENT CO., LTD., wherein a temperature has not been emended

EXAMPLE 1

Synthesization of
2-bromomethyl-3,5,6-trimethylpyrazine

1.1 Neutralization of Ligustrazine Hydrochloride

Weighing 50 g of ligustrazine hydrochloride salt and dissolving into 125 mL water, wherein the solution is clear and transparent, and pH is 3-4. Weighing 13.1 g NaOH and dissolving into 65 mL water, neutralizing the ligustrazine hydrochloride salt with the foregoing prepared 20% NaOH solution, keeping stirring, measuring pH, wherein white solid is separated out continuously, neutralizing until pH is about 8, processing with vacuum filtration to obtain a large amount of white solid, drying in an oven, 33.6 g white needle-like solid ligustrazine trihydrate is obtained, wherein a yield is 61.1%.

1.2 Preparation of Anhydrous Ligustrazine

Equation:

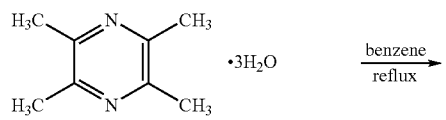 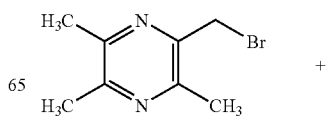 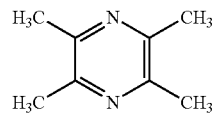

Reaction Steps:

Weighing 33.6 g of ligustrazine trihydrate and adding into a 250 mL flask, measuring 85 mL benzene and adding therein, heating to 150° C. with oil bath, processing circumfluence for 8 hours, stopping reaction, about 4.8 mL water is separated out, eliminating benzene with rotating distilling, wherein white solid is obtained, adding into an oven to dry, 20 g anhydrous ligustrazine is obtained, a yield is 83.3%, m.p. 85-87° C.

1.3 Synthesization of 2-bromomethyl-3,5,6-trimethylpyrazine

Equation:

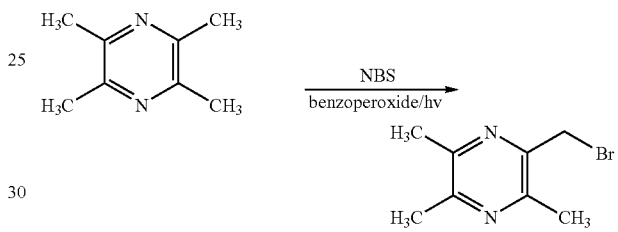

Reaction Steps:

Adding raw material of ligustrazine (20 g, 0.147 mol), NBS (26.75 g, 0.15 mol), benzoperoxide (0.05 g, 0.0002 mol), and CCl$_4$ (75 mL) into a 250 mL three-necked bottle in turn, wherein the solution appears orange and turbid, irradiating with incandescent lamp, heating to 75° C. with oil bath, processing circumfluence for 10 hours, wherein TLC [V(petroleum ether):V(ethyl acetate)=2:1 as developing agent] detecting shows that reaction is complete, (Rf of raw material=0.4, Rf of product=0.6), and the reaction solution appears purple, filtering out formed succinimide to obtain purple filtrate, recycling CCl$_4$ under reduced pressure to obtain a purple viscous liquid, distilling under reduced pressure, collecting a cut fraction under 99-101° C./2 mmHg to obtain 23 g colorless liquid of 2-bromomethyl-3,5,6-trimethylpyrazine, solidifying after cooling, m.p. 41.2-44° C., a yield is 72.8%.

EXAMPLE 2

Synthesization of 4-((3,5,6-trimethylpyrazine-2-yl)
methoxyl)-3,5-dimethoxybenzoic acid

2.1 Synthesization of 4-((3,5,6-trimethylpyrazine-2-yl)methoxyl)-3,5-dimethoxybenzoic acid ethyl ester Equation:

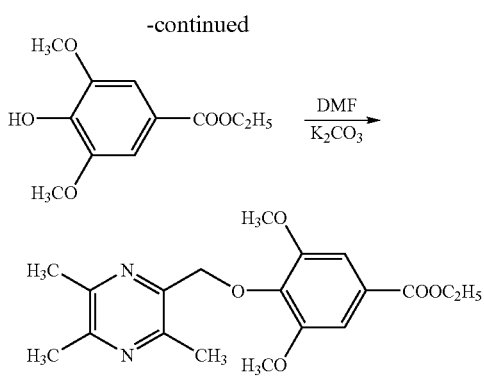

Reaction Steps:

Adding 2-bromomethyl-3,5,6-trimethylpyrazine (0.44 g, 0.002 mol), syringic acid ethyl ester (0.54 g, 0.0024 mol), anhydrous potassium carbonate (0.72 g, 0.005 mol), and DMF (20 mL) into a 100 mL three-necked bottle in turn, wherein the solution appears orange and turbid, irradiating with incandescent lamp, heating to 90° C., stifling to react for 12 hours, TLC [V(petroleum ether):V(ethyl acetate)=3:1 as developing agent] detecting shows that reaction is complete, (Rf of raw material=0.7, Rf of product=0.5), and the reaction solution appears deep yellow, filtering to obtain orange filtrate, adding 30 mL water, extracting with chloroform (3×30 mL), incorporating the chloroform layer and wishing with water (2×20 mL), drying with anhydrous sodium sulfate, recycling chloroform under reduced pressure to obtain a light yellow oily matter, separating with a silica column, wherein eluant is V(cyclohexane):V(ethyl acetate)=3:1, collecting product, recycling the solution under reduced pressure to obtain 0.45 g light yellow 4-((3,5,6-trimethylpyrazine-2-yl)methoxyl)-3,5-dimethoxybenzoic acid ethyl ester, a yield is 61.6%, m.p. 121.7-123.2° C.

$^1$H NMR (CDCl$_3$, 300 MHz) δ: 1.40 (t, 3H, J=7.1 Hz, —CH$_2$CH$_3$), 2.49 (s, 3H, 5'-CH$_3$), 2.52 (s, 3H, 6'-CH$_3$), 2.71 (s, 3H, 3'-CH$_3$), 3.86 (s, 6H, 2×-OCH$_3$), 4.38 (q, 2H, J=7.11 Hz, —CH$_2$CH$_3$), 5.16 (s, 2H, Ar—CH$_2$O—), 7.28 (s, 2H, 2×Ar—H); $^{13}$C NMR (CDCl$_3$, 75.5 MHz) δ: 166.3, 153.4, 151.1, 150.7, 148.5, 146.2, 140.6, 126.1, 106.7, 74.0, 61.3, 56.2, 21.7, 21.4, 20.6, 14.5; IR (KBr) v: 3108.0, 2985.8, 2948.7, 1708.3, 1594.2, 1462.1, 1415.5, 1332.1, 1250.0, 1220.4, 1126.6, 1029.6, 977.7, 761.8; ESI-Mass ($^+$c) for C$_{19}$H$_{24}$N$_2$O$_5$: m/z (M$^+$+H) 361.36.

2.2: Synthesization of 4-((3,5,6-trimethylpyrazine-2-yl)methoxyl)-3,5-dimethoxybenzoic acid Equation:

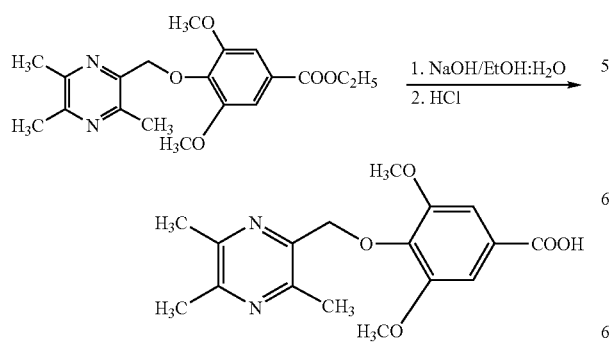

Reaction Steps:

Adding water (20 mL), NaOH (0.14 g, 3.5 mmol) into a 100 mL round-bottom flask, stirring to dissolve, then adding 95% alcohol (20 mL), 4-((3,5,6-trimethylpyrazine-2-yl)methoxyl)-3,5-dimethoxybenzoic acid ethyl ester (1.00 g, 2.8 mmol), stifling under room temperature to react for 4 hours, TLC [V(petroleum ether):V(ethyl acetate)=3:1 as developing agent] detecting shows that reaction is complete, (Rf of raw material=0.5, Rf of product=0), distilling out the alcohol under reduced pressure, adjusting pH of the reaction solution to 4-5 with 1.0M HCl while keeping the reaction solution cool to separate out solid, filtering, washing the solid with cool water for three times, processing with vacuum filtration, recrystallizing with anhydrous alcohol, drying under 70° C. for 8 hours to obtain 0.88 g white crystalloid of 4-((3,5,6-trimethylpyrazine-2-yl)methoxyl)-3,5-dimethoxybenzoic acid, wherein a yield is 95.4%, m.p.>218° C. (dec).

$^1$H NMR (DMSO-d$_6$, 300 MHz) δ: 2.40 (s, 3H, Ar—CH$_3$), 2.44 (s, 3H, Ar—CH$_3$), 2.59 (s, 3H, Ar—CH$_3$), 3.80 (s, 6H, 2×-OCH$_3$), 5.04 (s, 2H, Ar—CH$_2$O—), 7.22 (s, 2H, Ar—H); $^{13}$C NMR (DMSO-d$_6$, 75.5 MHz) δ: 166.8, 152.9, 150.7, 150.0, 147.8, 145.8, 139.9, 126.4, 106.6, 73.5, 56.0, 21.2, 20.8, 19.9; IR (KBr) v: 3441.6, 2934.7, 1712.3, 1592.1, 1503.8, 1459.3, 1412.2, 1325.5, 1220.2, 1177.0, 1129.3, 974.8, 852.7, 761.9, 700.6; ESI-Mass ($^-$c) for C$_{17}$H$_{20}$N$_2$O$_5$: m/z (M$^+$–H) 331.26.

EXAMPLE 3

Synthesization of 3-((3,5,6-trimethylpyrazine-2-yl)methoxyl)-4-methoxybenzoic acid 3.1 Synthesization of 3-((3,5,6-trimethylpyrazine-2-yl)methoxyl)-4-methoxybenzoic acid ethyl ester Equation:

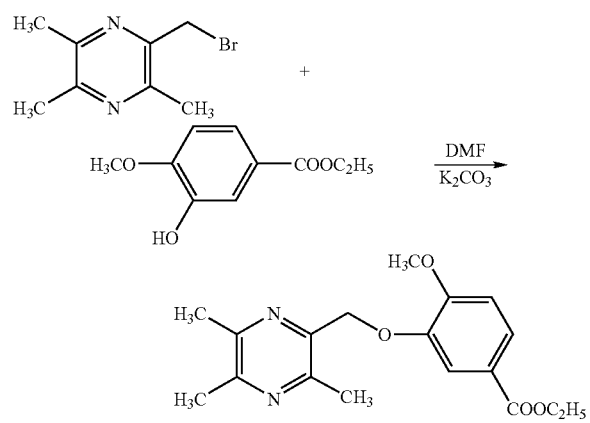

Reaction Steps:

Adding 2-bromomethyl-3,5,6-trimethylpyrazine (0.768 g, 0.003 mol), 3-hydroxy-4-methoxybenzoic acid ethyl ester (0.954 g, 0.005 mol), anhydrous potassium carbonate (1.1 g, 0.008 mol), and DMF (60 mL) into a 100 mL three-necked bottle in turn, wherein the solution appears orange, heating to 90° C. with oil bath, stirring to react for 12 hours, TLC [V(petroleum ether):V(ethyl acetate)=3:1 as developing agent] detecting shows that reaction is complete, (Rf of raw material=0.6, Rf of product=0.4), and the reaction solution appears orange, filtering to obtain orange filtrate, adding 30 mL water, extracting with chloroform (3×30 mL), incorporating the chloroform layer and wishing with water (2×20 mL), drying with anhydrous sodium sulfate, recycling chloroform under reduced pressure to obtain a light yellow oily matter, separating with a silica column, wherein eluant is V(petroleum ether):V(ethyl acetate)=3:1, collecting product, recycling the solution under reduced pressure to obtain light yellow solid, recrystallizing with anhydrous alcohol to obtain 0.71 g 3-((3,5,6-trimethylpyrazine-2-yl)methoxyl)-4-methoxybenzoic acid ethyl ester, a yield is 60.7%, m.p. 129.8-130.4° C.

$^1$H NMR (CDCl$_3$, 300 MHz) δ: 1.39 (t, 3H, J=7.11 Hz, —CH$_2$CH$_3$), 2.52 (s, 6H, 5',6'-CH$_3$), 2.62 (s, 3H, 3'-CH$_3$), 3.89 (s, 3H, —OCH$_3$), 4.36 (q, 2H, J=7.11 Hz, —CH$_2$CH$_3$), 5.24 (s, 2H, Ar—CH$_2$O—), 6.89 (d, 1H, J=8.37 Hz, Ar—H), 7.71 (d, 1H, J=8.37 Hz, Ar—H), 7.75 (s, 1H, Ar—H); $^{13}$C NMR (CDCl$_3$, 75.5 MHz) δ: 166.3, 153.7, 151.3, 150.1, 148.7, 147.6, 145.5, 124.3, 123.0, 115.0, 110.7, 71.0, 60.8, 56.0, 21.7, 21.4, 20.7, 14.5; IR (KBr) ν: 3089.1, 2979.7, 2843.2, 1715.8, 1601.0, 1517.8, 1416.4, 1269.0, 1218.6, 1177.7, 1125.7, 1022.0, 870.0, 837.6, 757.9; ESI-Mass ($^+$c) for C$_{18}$H$_{22}$N$_2$O$_4$: m/z (M$^+$+H) 331.31.

3.2 Synthesization of 3-((3,5,6-trimethylpyrazine-2-yl)methoxyl)-4-methoxybenzoic acid Equation:

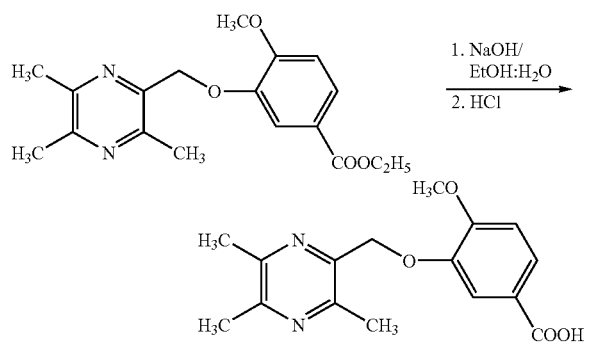

Reaction Steps:
Adding water (20 mL), NaOH (0.14 g, 3.5 mmol) into a 100 mL round-bottom flask, stirring to dissolve, then adding 95% alcohol (20 mL), 4-((3,5,6-trimethylpyrazine-2-yl)methoxyl)-4-methoxybenzoic acid ethyl ester (0.90 g, 2.7 mmol), stirring under room temperature to react for 4 hours, TLC [V(petroleum ether):V(ethyl acetate)=3:1 as developing agent] detecting shows that reaction is complete, (Rf of raw material=0.4, Rf of product=0), distilling out the alcohol under reduced pressure, adjusting pH of the reaction solution to 4-5 with 1.0M HCl while keeping the reaction solution cool to separate out solid, filtering, washing the solid with cool water for three times, processing with vacuum filtration, recrystallizing with anhydrous alcohol, drying under 70° C. for 8 hours to obtain 0.76 g white crystalloid of 3-((3,5,6-trimethylpyrazine-2-yl)methoxyl)-4-methoxybenzoic acid, wherein a yield is 92.7%, m.p. 190-192° C.

$^1$H NMR (DMSO-d$_6$, 300 MHz) δ: 2.47 (s, 3H, Ar—CH$_3$), 2.48 (s, 3H, Ar—CH$_3$), 2.52 (s, 3H, Ar—CH$_3$), 3.83 (s, 3H, Ar—OCH$_3$), 5.19 (s, 2H, Ar—CH$_2$O—), 7.08 (d, 1H, J=8.52 Hz, Ar—H), 7.61 (d, 1H, J=8.52 Hz, Ar—H), 7.66 (d, 1H, J=1.50 Hz, Ar—H), 12.66 (brs, 1H, —COOH); $^{13}$C NMR (DMSO-d$_6$, 75.5 MHz) δ: 167.0, 153.0, 151.0, 149.5, 148.2, 147.2, 145.2, 123.8, 122.9, 114.2, 111.3, 70.1, 55.7, 21.2, 20.9, 20.1; IR (KBr) ν: 3425.1, 2943.4, 1681.4, 1598.0, 1517.5, 1443.1, 1305.7, 1271.4, 1228.2, 1136.0, 1022.8, 826.1, 764.1; ESI-Mass ($^+$c) for C$_{16}$H$_{18}$N$_2$O$_4$: m/z (M$^+$+H) 302.33.

EXAMPLE 4

Synthesization of 4-((3,5,6-trimethylpyrazine-2-yl)methoxyl)benzoic acid 4.1 4-((3,5,6-trimethylpyrazine-2-yl)methoxyl)benzoic acid ethyl ester Equation:

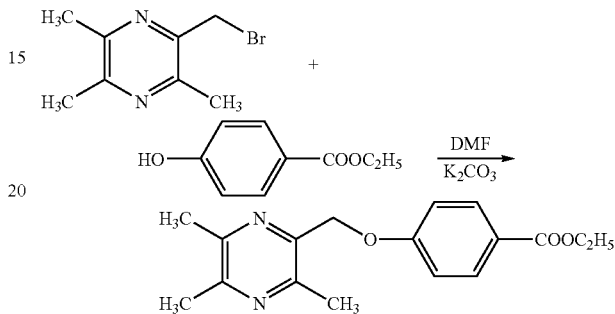

Reaction Steps:
Adding 2-bromomethyl-3,5,6-trimethylpyrazine (0.86 g, 0.0040 mol), ethyl p-hydroxybenzoate (0.948 g, 0.0057 mol), anhydrous potassium carbonate (1.38 g, 0.0103 mol), and DMF (60 mL) into a 100 mL three-necked bottle in turn, heating to 85° C. with oil bath, stirring to react for 12 hours, TLC [V(cyclohexane):V(ethyl acetate)=3:1 as developing agent] detecting shows that reaction is complete, (Rf of raw material=0.5, Rf of product=0.4), and the reaction solution appears yellow, filtering to obtain yellow filtrate, adding 30 mL water, extracting with chloroform (3×30 mL), incorporating the chloroform layer and wishing with water (2×20 mL), drying with anhydrous sodium sulfate, recycling chloroform under reduced pressure to obtain a light yellow oily matter, separating with a silica column, wherein eluant is V(cyclohexane):V(ethyl acetate)=3:1, collecting product, rotating distilling to obtain light yellow solid, recrystallizing with anhydrous alcohol to obtain 0.76 g 4-((3,5,6-trimethylpyrazine-2-yl)methoxyl)benzoic acid ethyl ester, a yield is 63.3%, m.p. 75.0-75.7° C.

$^1$H NMR (CDCl$_3$, 300 MHz) δ: 1.38 (t, 3H, J=7.11 Hz, —CH$_2$CH$_3$), 2.53 (s, 6H, 5',6'-CH$_3$), 2.59 (s, 3H, 3'-CH$_3$), 4.35 (q, 2H, J=7.11 Hz, —CH$_2$CH$_3$), 5.21 (s, 2H, Ar—CH$_2$O—), 7.03 (d, 2H, J=8.75 Hz, Ar—H), 8.00 (d, 2H, J=8.75 Hz, Ar—H); $^{13}$C NMR (CDCl$_3$, 75.5 MHz) δ: 166.3, 162.3, 151.6, 150.0, 148.8, 145.2, 131.6, 123.5, 114.5, 70.1, 60.7, 21.8, 21.5, 20.7, 14.5; IR (KBr) ν: 3085.2, 2975.7, 2933.5, 1705.9, 1604.4, 1507.5, 1461.9, 1415.3, 1278.8, 1236.0, 1167.3, 1104.6, 1018.1, 852.1, 766.3; ESI-Mass ($^+$c) for C$_{17}$H$_{20}$N$_2$O$_3$: m/z (M$^+$+H) 301.34.

4.2 Synthesization of 4-((3,5,6-trimethylpyrazine-2-yl)methoxyl)benzoic acid

Equation:

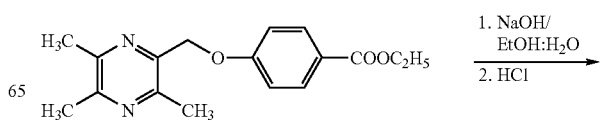

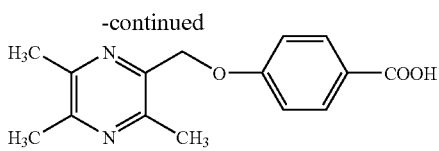

Reaction Steps:

Adding water (20 mL), NaOH (0.14 g, 3.5 mmol) into a 100 mL round-bottom flask, stirring to dissolve, then adding 95% alcohol (20 mL), 4-((3,5,6-trimethylpyrazine-2-yl)methoxyl)benzoic acid ethyl ester (0.90 g, 3.0 mmol), stirring under room temperature to react for 4 hours, TLC [V(petroleum ether):V(ethyl acetate)=3:1 as developing agent] detecting shows that reaction is complete, (Rf of raw material=0.4, Rf of product=0), distilling out the alcohol under reduced pressure, adjusting pH of the reaction solution to 4-5 with 6.0M HCl while keeping the reaction solution cool to separate out solid, filtering, washing the solid with cool water for three times, processing with vacuum filtration, recrystallizing with anhydrous alcohol, drying under 70° C. for 8 hours to obtain 0.73 g white crystalloid of 4-((3,5,6-trimethylpyrazine-2-yl)methoxyl)benzoic acid, wherein a yield is 89.8%, m.p. 179-181° C.

$^1$H NMR (DMSO-d$_6$, 300 MHz) δ: 2.45 (s, 3H, Ar—CH$_3$), 2.50 (s, 3H, Ar—CH$_3$), 2.56 (s, 3H, Ar—CH$_3$), 5.23 (s, 2H, Ar—CH$_2$O—), 7.12 (d, 2H, J=8.67 Hz, Ar—H), 7.89 (d, 2H, J=8.67 Hz, Ar—H), 12.63 (brs, 1H, —COOH); $^{13}$C NMR (DMSO-d$_6$, 75.5 MHz) δ: 166.9, 161.9, 151.1, 149.3, 148.4, 144.9, 131.3, 123.4, 114.6, 69.4, 21.2, 20.9, 20.1; IR (KBr) ν: 2920.0, 1703.2, 1604.1, 1509.5, 1418.7, 1260.3, 1211.0, 1168.7, 1107.2, 1019.3, 851.9, 810.7, 772.7; ESI-Mass ($^+$c) for C$_{15}$H$_{16}$N$_2$O$_3$: m/z (M$^+$+H) 273.06.

EXAMPLE 5

Synthesization of 4-((3,5,6-trimethylpyrazine-2-yl)methoxyl)-3-methoxybenzoic acid

5.1 4-((3,5,6-trimethylpyrazine-2-yl)methoxyl)-3-methoxybenzoic methyl ester Equation:

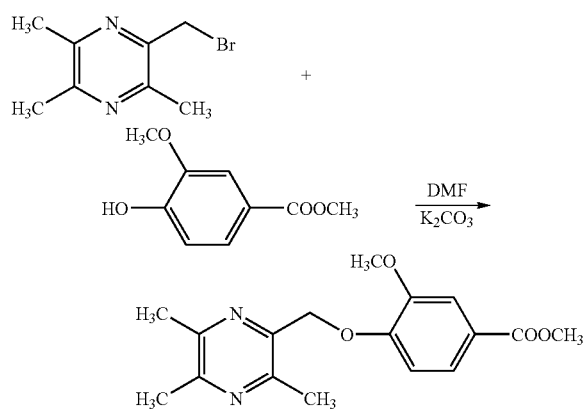

Reaction Steps:

Adding 2-bromomethyl-3,5,6-trimethylpyrazine (0.5 g, 2.33 mmol), methyl vanillate (0.6 g, 3.30 mmol), anhydrous potassium carbonate (1.0 g, 7.25 mmol), and DMF (40 mL) into a 100 mL three-necked bottle in turn, heating to 85° C. with oil bath, stifling to react for 8 hours, TLC [V(cyclohexane):V(ethyl acetate)=3:1 as developing agent] detecting shows that reaction is complete, (Rf of raw material=0.6, Rf of product=0.35), filtering to obtain filtrate, adding 30 mL water, extracting with chloroform (3×30 mL), incorporating the chloroform layer and wishing with water (2×20 mL), drying with anhydrous sodium sulfate, recycling chloroform under reduced pressure to obtain a light yellow oily matter, separating with a silica column, wherein eluant is V(petroleum ether):V(ethyl acetate)=3:1, collecting product, recycling the solution under reduced pressure to obtain solid, 0.51 g white crystalloid of 4-((3,5,6-trimethylpyrazine-2-yl)methoxyl)-3-methoxybenzoic methyl ester, a yield is 69.3%, m.p. 129.8-130.4° C.

$^1$H NMR (CDCl$_3$, 300 MHz) δ: 2.52 (s, 6H, 5',6'-CH$_3$), 2.62 (s, 3H, 3'-CH$_3$), 3.89 (s, 6H, —OCH$_3$, —COOCH$_3$), 5.27 (s, 2H, Ar—CH$_2$O—), 7.07 (d, 1H, J=8.46 Hz, Ar—H), 7.55 (s, 1H, Ar—H), 7.65 (d, 1H, J=8.46 Hz, Ar—H); $^{13}$C NMR (CDCl$_3$, 75.5 MHz) δ: 166.9, 152.1, 151.5, 150.2, 149.3, 148.7, 145.2, 123.4, 123.3, 112.9, 112.6, 70.9, 56.1, 52.1, 21.8, 21.5, 20.8; IR (KBr) ν: 3081.9, 2985.8, 2951.7, 1714.5, 1597.9, 1515.2, 1452.8, 1415.5, 1295.4, 1275.6, 1230.6, 1182.0, 1107.5, 1039.9, 991.0, 874.0, 836.0, 760.1; ESI-Mass ($^+$c) for C$_{17}$H$_{20}$N$_2$O$_4$: m/z (M$^+$+H) 317.39.

5.2 Synthesization of 4-((3,5,6-trimethylpyrazine-2-yl)methoxyl)-3-methoxybenzoic acid Equation:

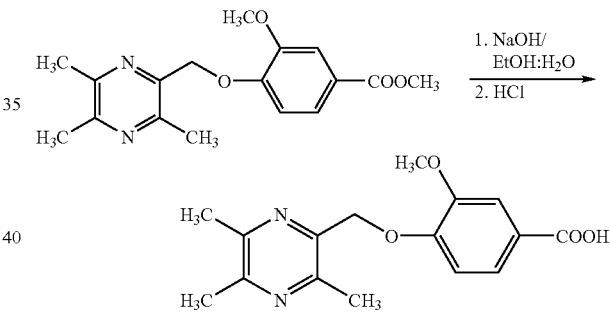

Reaction Steps:

Adding water (20 mL), NaOH (0.14 g, 3.5 mmol) into a 100 mL round-bottom flask, stirring to dissolve, then adding 95% alcohol (20 mL), 4-((3,5,6-trimethylpyrazine-2-yl)methoxyl)-4-methoxybenzoic acid methyl ester (0.89 g, 2.8 mmol), stifling under room temperature to react for 4 hours, TLC [V(petroleum ether):V(ethyl acetate)=3:1 as developing agent] detecting shows that reaction is complete, (Rf of raw material=0.35, Rf of product=0), distilling out the alcohol under reduced pressure, adjusting pH of the reaction solution to 4-5 with 6.0M HCl while keeping the reaction solution cool to separate out solid, filtering, washing the solid with cool water for three times, processing with vacuum filtration, recrystallizing with anhydrous alcohol, drying under 70° C. for 8 hours to obtain 0.75 g white crystalloid of 4-((3,5,6-trimethylpyrazine-2-yl)methoxyl)-3-methoxybenzoic acid, wherein a yield is 92.6%, m.p. 183-185° C.

$^1$H NMR (DMSO-d$_6$, 300 MHz) δ: 2.46 (s, 3H, Ar—CH$_3$), 2.47 (s, 3H, Ar—CH$_3$), 2.51 (s, 3H, Ar—CH$_3$), 3.80 (s, 3H, Ar—OCH$_3$), 5.22 (s, 2H, Ar—CH$_2$O—), 7.22 (d, 1H, J=8.45 Hz, Ar—H), 7.47 (d, 1H, J=1.57 Hz, Ar—H), 7.56 (d, 1H, J=8.45 Hz, Ar—H); $^{13}$C NMR (DMSO-d$_6$, 75.5 MHz) δ: 167.2, 151.5, 151.2, 149.5, 148.7, 148.4, 145.0, 123.9, 122.9, 112.7, 112.3, 70.1, 55.6, 21.3, 20.9, 20.1; IR (KBr) v: 3497.2, 2937.6, 1695.0, 1596.9, 1514.9, 1457.5, 1421.8, 1384.7, 1263.1, 1215.0, 1180.4, 1147.6, 1109.7, 1029.1, 872.9, 767.5, 741.4; ESI-Mass (⁻c) for $C_{16}H_{18}N_2O_4$: m/z ($M^+$−H) 301.33.

EXAMPLE 6

Synthesization of (E)-3-(4-((3,5,6-Trimethylpyrazin-2-yl)methoxy)-3-methoxyphenyl)acrylic acid

6.1 Synthesization of (E)-3-(4-((3,5,6-Trimethylpyrazin-2-yl)methoxy)-3-methoxyphenyl)acrylic acid ethyl ester Equation:

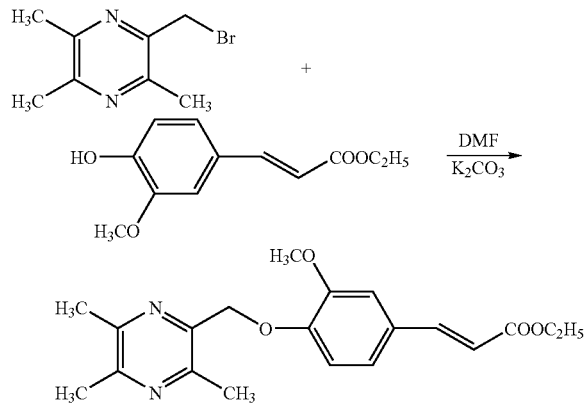

Reaction Steps:

Adding 2-bromomethyl-3,5,6-trimethylpyrazine (0.5 g, 3.02 mmol), ferulic acid ethyl ester (0.97 g, 4.37 mmol), anhydrous potassium carbonate (1.0 g, 7.25 mmol), and DMF (40 mL) into a 100 mL three-necked bottle in turn, heating to 85° C. with oil bath, stirring to react for 8 hours, TLC [V(cyclohexane):V(ethyl acetate)=3:1 as developing agent] detecting shows that reaction is complete, (Rf of raw material=0.6, Rf of product=0.5), filtering to obtain filtrate, adding 30 mL water, extracting with chloroform (3×30 mL), incorporating the chloroform layer and wishing with water (2×20 mL), drying with anhydrous sodium sulfate, recycling chloroform under reduced pressure to obtain a light yellow oily matter, separating with a silica column, wherein eluant is V(petroleum ether):V(ethyl acetate)=3:1, collecting product, recycling the solution under reduced pressure to obtain solid, 0.75 g (E)-3-(4-((3,5,6-Trimethylpyrazin-2-yl)methoxy)-3-methoxyphenyl)acrylic acid ethyl ester, a yield is 69.7%, m.p. 111.5-111.9° C.

$^1$H NMR (CDCl$_3$, 300 MHz) δ: 1.34 (t, 3H, J=7.11 Hz, —CH$_2$CH$_3$), 2.52 (s, 6H, 5',6'-CH$_3$), 2.65 (s, 3H, 3'-CH$_3$), 3.87 (s, 3H, —OCH$_3$), 4.26 (q, 2H, J=7.11 Hz, —CH$_2$CH$_3$), 5.24 (s, 2H, Ar—CH$_2$O—), 6.31 (d, 1H, J=15.9 Hz, =CH—), 7.05 (m, 3H, Ar—H), 7.62 (d, 1H, J=15.9 Hz, Ar—CH=); $^{13}$C NMR (CDCl$_3$, 75.5 MHz) δ: 167.1, 151.3, 150.2, 150.1, 149.9, 148.5, 145.4, 144.4, 128.2, 122.3, 116.3, 113.8, 110.3, 70.9, 60.4, 56.0 55.9, 21.7, 21.4, 20.7, 14.4; IR (KBr) v: 3079.2, 2995.2, 2932.8, 1703.1, 1635.9, 1590.9, 1508.4, 1460.0, 1416.7, 1305.0, 1260.4, 1179.8, 1138.4, 994.0, 836.9, 806.9; ESI-Mass (⁺c) for $C_{20}H_{24}N_2O_4$: m/z ($M^+$+H) 357.39.

6.2 Synthesization of (E)-3-(4-((3,5,6-Trimethylpyrazin-2-yl)methoxy)-3-methoxyphenyl)acrylic acid Equation:

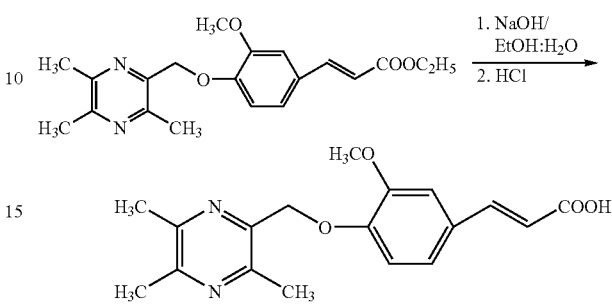

Reaction Steps:

Adding water (20 mL), NaOH (0.14 g, 3.5 mmol) into a 100 mL round-bottom flask, stirring to dissolve, then adding 95% alcohol (20 mL), (E)-3-(4-((3,5,6-Trimethylpyrazin-2-yl) methoxy)-3-methoxyphenyl)acrylic acid ethyl ester (1.0 g, 2.8 mmol), stifling under room temperature to react for 4 hours, TLC [V(petroleum ether):V(ethyl acetate)=3:1 as developing agent] detecting shows that reaction is complete, (Rf of raw material=0.5, Rf of product=0), distilling out the alcohol under reduced pressure, adjusting pH of the reaction solution to 4-5 with 6.0M HCl while keeping the reaction solution cool to separate out solid, filtering, washing the solid with cool water for three times, processing with vacuum filtration, recrystallizing with anhydrous alcohol, drying under 70° C. for 8 hours to obtain 0.87 g white crystalloid of (E)-3-(4-((3,5,6-Trimethylpyrazin-2-yl)methoxy)-3-methoxyphenyl)acrylic acid, wherein a yield is 94.6%, m.p. 156-158° C.

$^1$H NMR (DMSO-d$_6$, 300 MHz) δ: 2.45 (s, 3H, Ar—CH$_3$), 2.46 (s, 3H, Ar—CH$_3$), 2.49 (s, 3H, Ar—CH$_3$), 3.79 (s, 3H, Ar—OCH$_3$), 5.17 (s, 2H, Ar—CH$_2$O—), 6.46 (d, 1H, J=15.9 Hz, =CH—), 7.13 (d, 1H, J=8.28 Hz, Ar—H), 7.21 (d, 1H, J=8.28 Hz, Ar—H), 7.33 (s, 1H, Ar—H), 7.52 (d, 1H, J=15.9 Hz, ArCH=), 12.22 (brs, 1H, —COOH); $^{13}$C NMR (DMSO-d$_6$, 75.5 MHz) δ: 167.8, 151.1, 149.7, 149.5, 149.3, 148.3, 145.2, 143.9, 127.7, 122.4, 117.1, 113.4, 110.8, 70.1, 55.7, 21.2, 20.9, 20.1; IR (KBr) v: 3399.8, 2926.3, 1689.0, 1628.8, 1595.0, 1514.0, 1419.1, 1263.8, 1209.0, 1169.2, 1140.8, 1036.0, 983.4, 843.1, 806.1; ESI-Mass (⁻c) for $C_{20}H_{24}N_2O_4$: m/z ($M^+$−H) 327.28.

EXAMPLE 7

Synthesization of (E)-3-(4-((3,5,6-Trimethylpyrazin-2-yl)methoxy)-phenyl)acrylic acid

7.1 Synthesization of (E)-3-(4-((3,5,6-Trimethylpyrazin-2-yl)methoxy)-phenyl)acrylic acid ethyl ester Equation:

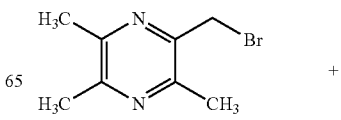

-continued

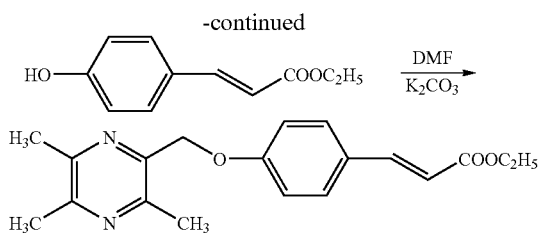

Reaction Steps:

Adding 2-bromomethyl-3,5,6-trimethylpyrazine (2.15 g, 0.01 mol), p-hydroxyl ethyl cinnamate (2.30 g, 0.012 mol), anhydrous potassium carbonate (2.76 g, 0.02 mol), and DMF (50 mL) into a 100 mL three-necked bottle in turn, heating to 90° C., stifling to react for 10 hours, TLC [V(petroleum ether):V(ethyl acetate)=3:1 as developing agent] detecting shows that reaction is complete, (Rf of raw material=0.6, Rf of product=0.5), filtering to obtain filtrate, adding 40 mL water, extracting with chloroform (3×40 mL), incorporating the chloroform layer and wishing with water (2×30 mL), drying with anhydrous sodium sulfate, recycling chloroform under reduced pressure to obtain a light yellow oily matter, separating with a silica column, wherein eluant is V(petroleum ether):V(ethyl acetate)=3:1, collecting product, recycling the solution under reduced pressure to obtain 2.5 g white crystalloid of (E)-3-(4-((3,5,6-Trimethylpyrazin-2-yl)methoxy)-phenyl)acrylic acid ethyl ester, a yield is 76.7%, m.p. 90-92° C.

$^1$H NMR (CDCl$_3$, 300 MHz) δ: 1.26 (t, 3H, J=7.11 Hz, —CH$_2$CH$_3$), 2.45 (s, 6H, 5',6'-CH$_3$), 2.51 (s, 3H, 3'-CH$_3$), 4.18 (q, 2H, J=7.11 Hz, —CH$_2$CH$_3$), 5.11 (s, 2H, Ar—CH$_2$O—), 6.24 (d, 1H, J=16.01 Hz, =CH—), 6.94 (d, 2H, J=8.69 Hz, Ar—H), 7.40 (d, 2H, J=8.69 Hz, Ar—H), 7.56 (d, 1H, J=16.01 Hz, Ar—CH=); $^{13}$C NMR (CDCl$_3$, 75.5 MHz) δ: 167.2, 160.3, 151.5, 149.9, 148.6, 145.2, 144.1, 129.7, 127.7, 116.1, 115.2, 70.0, 60.3, 21.7, 21.4, 20.6, 14.4; IR (KBr) v: 3044.6, 2969.5, 1703.4, 1630.6, 1601.0, 1513.0, 1417.0, 1292.8, 1244.5, 1166.8, 1008.9, 980.1, 828.4, 796.4; ESI-Mass (+0 for C$_{19}$H$_{22}$N$_2$O$_3$: m/z (M$^+$+H) 327.17.

Synthesization of (E)-3-(4-((3,5,6-Trimethylpyrazin-2-yl)methoxy)-phenyl)acrylic acid Equation:

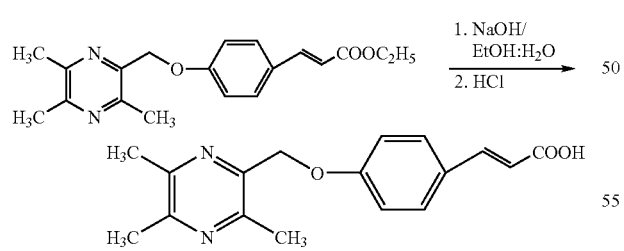

Reaction Steps:

Adding water (20 mL), NaOH (0.14 g, 3.5 mmol) into a 100 mL round-bottom flask, stirring to dissolve, then adding 95% alcohol (20 mL), (E)-3-(4-((3,5,6-Trimethylpyrazin-2-yl)methoxy)-phenyl)acrylic acid ethyl ester (1.0 g, 3.07 mmol), stifling under room temperature to react for 4 hours, TLC [V(petroleum ether):V(ethyl acetate)=3:1 as developing agent] detecting shows that reaction is complete, (Rf of raw material=0.5, Rf of product=0), distilling out the alcohol under reduced pressure, adjusting pH of the reaction solution to 4-5 with 6.0M HCl while keeping the reaction solution cool to separate out solid, filtering, washing the solid with cool water for three times, processing with vacuum filtration, recrystallizing with anhydrous alcohol, drying under 70° C. for 8 hours to obtain 0.85 g white crystalloid of (E)-3-(4-((3,5,6-Trimethylpyrazin-2-yl)methoxy)-phenyl)acrylic acid, wherein a yield is 93.0%, m.p. 152-154° C.

What is claimed is:

1. A compound of formula I, or a medicinally acceptable salt thereof:

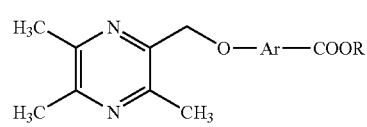

wherein Ar is selected from the group consisting of phenyl, 3,5-dimethoxyphenyl, 3-methoxyphenyl, 4-methoxyphenyl, styryl, and 3-methoxy styryl, and R is H.

2. The compound, as recited in claim 1, or a medicinally acceptable salt thereof, wherein the medicinally acceptable salt is selected from the group consisting of alkali metal salts, and alkaline-earth metal salts.

3. The compound, as recited in claim 1, or a medicinally acceptable salt thereof, wherein the medicinally acceptable salt is selected from the group consisting of potassium, sodium, ammonium, hydrochloride, sulfate, citrate and maleate.

4. The compound, as recited in claim 1, wherein the compound is selected from the group consisting of:
4-((3,5,6-trimethylpyrazine-2-yl)methoxyl)benzoic acid,
(E)-3-(4-((3,5,6-trimethylpyrazin-2-yl)methoxy)-3-methoxyphenyl)acrylic acid, and
3-((3,5,6-trimethylpyrazin-2-yl)methoxy)-4-methoxybenzoic acid,
or a medicinally acceptable salt thereof.

5. A method of treating platelet aggregation in a mammal, comprising the step of: applying a therapeutically effective amount of a compound according to claim 1, or a medicinally acceptable salt thereof, to said mammal.

6. A process for preparing a compound according to claim 1, or a medicinally acceptable salt thereof, comprising the steps of:
a) reacting 2-bromomethyl-3,5,6-trimethylpyrazine with a compound selected from the group consisting of HO—Ar—COOR, wherein R is —CH$_3$, or —CH$_2$CH$_3$, and HO—Ar—CHO, to obtain an intermediate, selected from the group consisting of

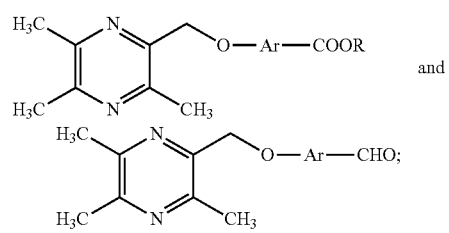

and b) reacting the intermediate obtained in step a) to obtain a compound according to claim 1; and
c) optionally converting the compound according to claim 1 to a medicinally acceptable salt thereof.

7. The process, as recited in claim 6, wherein step a) further comprises:
i. dissolving HO—Ar—COOR or HO—Ar—CHO and 2-bromomethyl-3,5, 6-trimethylpyrazine in an organic solvent selected from the group consisting of N,N-dimethylformamide and acetone; and
ii. adding a base selected from the group consisting of K₂CO₃, Na₂CO₃, and Et₃N.

8. The process, as recited in claim 6, wherein step b) further comprises:
i. dissolving

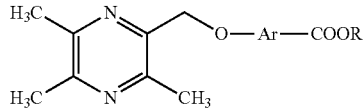

in a solvent selected from the group consisting of alcohol and methanol-water, and
ii. adding a base selected from the group consisting of NaOH and KOH.

9. The process, as recited in claim 6, wherein step b) comprises:
i. mixing

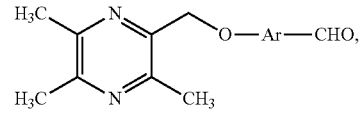

malonic acid, pyridine, benzene, and piperidine.

10. The process, as recited in claim 6, wherein step a) further comprises:
i. dissolving HO—Ar—COOR and 2-bromomethyl-3,5,6-trimethylpyrazine in an organic solvent selected from the group consisting of N,N-dimethylformamide and acetone; and
ii. adding a base selected from the group consisting of K₂CO₃, Na₂CO₃, and Et₃N;
and step b) further comprises:
iii. dissolving

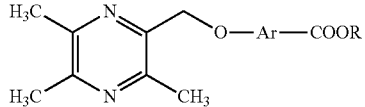

in a solvent selected from the group consisting of alcohol and methanol-water, and
iv. adding a base selected from the group consisting of NaOH and KOH.

11. The process, as recited in claim 6, wherein step a) further comprises:
i. dissolving HO—Ar—CHO and 2-bromomethyl-3,5,6-trimethylpyrazine in an organic solvent selected from the group consisting of N,N-dimethylformamide and acetone; and
ii. adding a base selected from the group consisting of K₂CO₃, Na₂CO₃, and Et₃N;
and step b) further comprises:
iii. mixing

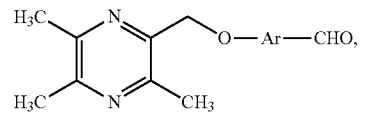

malonic acid, pyridine, benzene, and piperidine.

* * * * *